US009823124B2

(12) United States Patent
Clerici et al.

(10) Patent No.: US 9,823,124 B2
(45) Date of Patent: Nov. 21, 2017

(54) FULLY-COHERENT TERAHERTZ DETECTION METHOD AND SYSTEM

(71) Applicants: INSTITUT NATIONAL DE LA RECHERCHE SCIENTIFIQUE, Quebec (CA); HERIOT WATT UNIVERSITY, Edinburgh (GB)

(72) Inventors: Matteo Clerici, Balerno (GB); Marco Peccianti, Brighton (GB); Sze Phing Ho, Kedah (MY); Anna Mazhorova, Verdun (CA); Roberto Morandotti, Montreal (CA); Alessia Pasquazi, Brighton (GB); Luca Razzari, Montreal (CA); Yoann Jestin, Montreal (CA)

(73) Assignee: INSTITUT NATIONAL DE LA RECHERCHE SCIENTIFIQUE, Québec (CA)

( * ) Notice: Subject to any disclaimer, the term of this patent is extended or adjusted under 35 U.S.C. 154(b) by 0 days.

(21) Appl. No.: 15/302,802

(22) PCT Filed: Apr. 8, 2015

(86) PCT No.: PCT/CA2015/050285
§ 371 (c)(1),
(2) Date: Oct. 7, 2016

(87) PCT Pub. No.: WO2015/154184
PCT Pub. Date: Oct. 15, 2015

(65) Prior Publication Data
US 2017/0030770 A1    Feb. 2, 2017

Related U.S. Application Data

(60) Provisional application No. 61/977,736, filed on Apr. 10, 2014.

(51) Int. Cl.
*G01J 1/44* (2006.01)
*G01J 5/02* (2006.01)
(Continued)

(52) U.S. Cl.
CPC .............. *G01J 1/44* (2013.01); *G01J 5/024* (2013.01); *G01J 5/20* (2013.01); *G01N 21/3581* (2013.01); *G01R 29/00* (2013.01)

(58) Field of Classification Search
CPC .... G01J 1/44; G01J 5/024; G01J 5/20; G01N 21/3581; G01R 29/00
See application file for complete search history.

(56) References Cited

U.S. PATENT DOCUMENTS

| 7,480,434 B2 | 1/2009 | Hochberg et al. | |
| 8,629,423 B1 * | 1/2014 | Kislov | H01L 31/1085 250/214.1 |

(Continued)

OTHER PUBLICATIONS

A. Nahata et al., Detection of freely propagating teragertz radiation by use of optical second-harmonic generation, Optics Letters, 1998, pp. 67-69, vol. 23, No. 1, Optical Society of America, U.S.A.
(Continued)

*Primary Examiner* — David Porta
*Assistant Examiner* — Mindy Vu

(57) ABSTRACT

A method and a system for terahertz detection, using at least a first and a second electrodes separated by a centro-symmetric material. The system comprises at least a first and a second electrodes with conductive pads for connection to a voltage source, separated by a centro-symmetric material; the method comprising second harmonic generation in the centro-symmetric material by overlapping of a probe and a terahertz beams.

14 Claims, 4 Drawing Sheets

(51) Int. Cl.
G01J 5/20 (2006.01)
G01R 29/00 (2006.01)
G01N 21/3581 (2014.01)

(56) References Cited

U.S. PATENT DOCUMENTS

| | | | |
|---|---|---|---|
| 2005/0100866 A1 | 5/2005 | Arnone et al. | |
| 2005/0116861 A1* | 6/2005 | Anazawa | B82Y 10/00 343/700 MS |
| 2012/0146743 A1* | 6/2012 | Ermolov | B82Y 10/00 333/161 |
| 2012/0318983 A1 | 12/2012 | Ouchi | |
| 2013/0222788 A1* | 8/2013 | Kajiki | G01B 11/303 356/51 |
| 2014/0061469 A1 | 3/2014 | Hwang et al. | |

OTHER PUBLICATIONS

D. Grischkowsky et al., Far-infrared time-domain spectroscopy with terahertz beams of dielectics and semiconductors, Journal Optical Society of America, 1990, pp. 2006-2015, vol. 7, No. 10, Optical Society of America, U.S.A.

Q. Wu et al, Broadband detection capability of ZnTe electro-optic field detectors, Apply Physics Letters, 1996, pp. 2924-2926, vol. 68, AIP Publishing, U.S.A.

C. Ohlhoff, Optical second-harmonic probe for silicon millimeter-wave circuits, Apply Physics Letters, 1996, pp. 1699-1701, vol. 68, AIP Publishing, U.S.A.

D.J. Cook, Terahertz-field-induced second-harmonic generation measurements of liquid dynamics, Chemical Physics Letters, 1999, pp. 221-228, vol. 309, Elsevier Science B.V., Nederland.

J. Dai et al., Detection of Broadband Terahertz Waves with a Laser-Induced Plasma in Gases, Physical Review Letters, 2006, pp. 103903-1-to 103903-4, vol. 97, The American Physical Society, U.S.A.

N. Karpowicz et al., Coherent heterodyne time-domain spectrometry covering the entire "terahertz gap", Applied Physics Letters, 2008, pp. 11131-1 to 11131-3, vol. 92, AIP Publishing, U.S.A.

Chia-Yeh Li et al., Coherent Detection of Terahertz via Laser Induced Plasma with Controlled Optical Bias, Technical Digest, 2013, CLEO Cnference: Science and Innovations, U.S.A.

M. Clerici et al., Spectrally resolved wave-mixing between near- and far-infrared pulses in gas, New Journal of Physics, 2013, pp. 1-13, vol. 15, IOP Publishing Ltd and Deutsche Physikalische Gesellschaft, U.S.A.

* cited by examiner

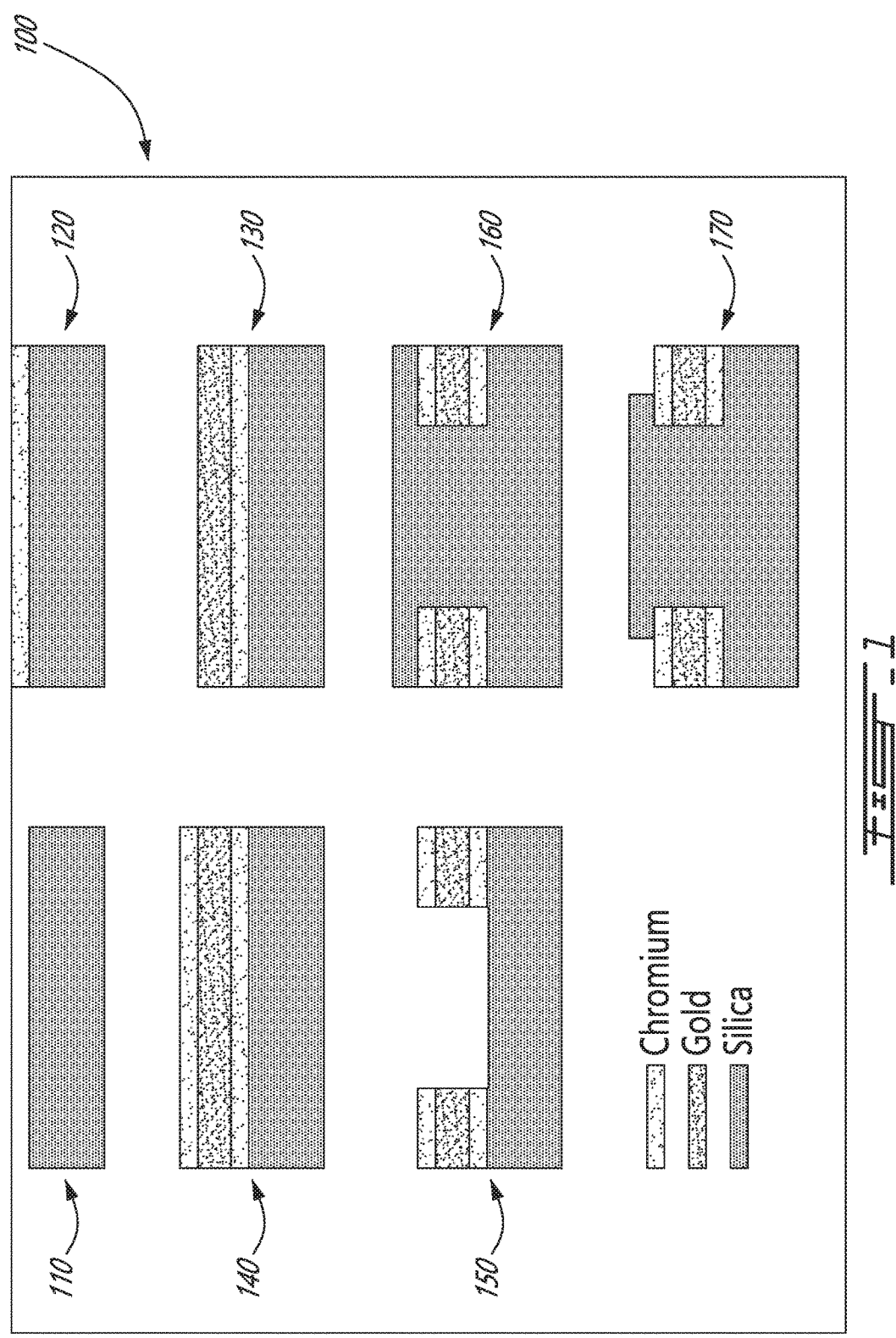

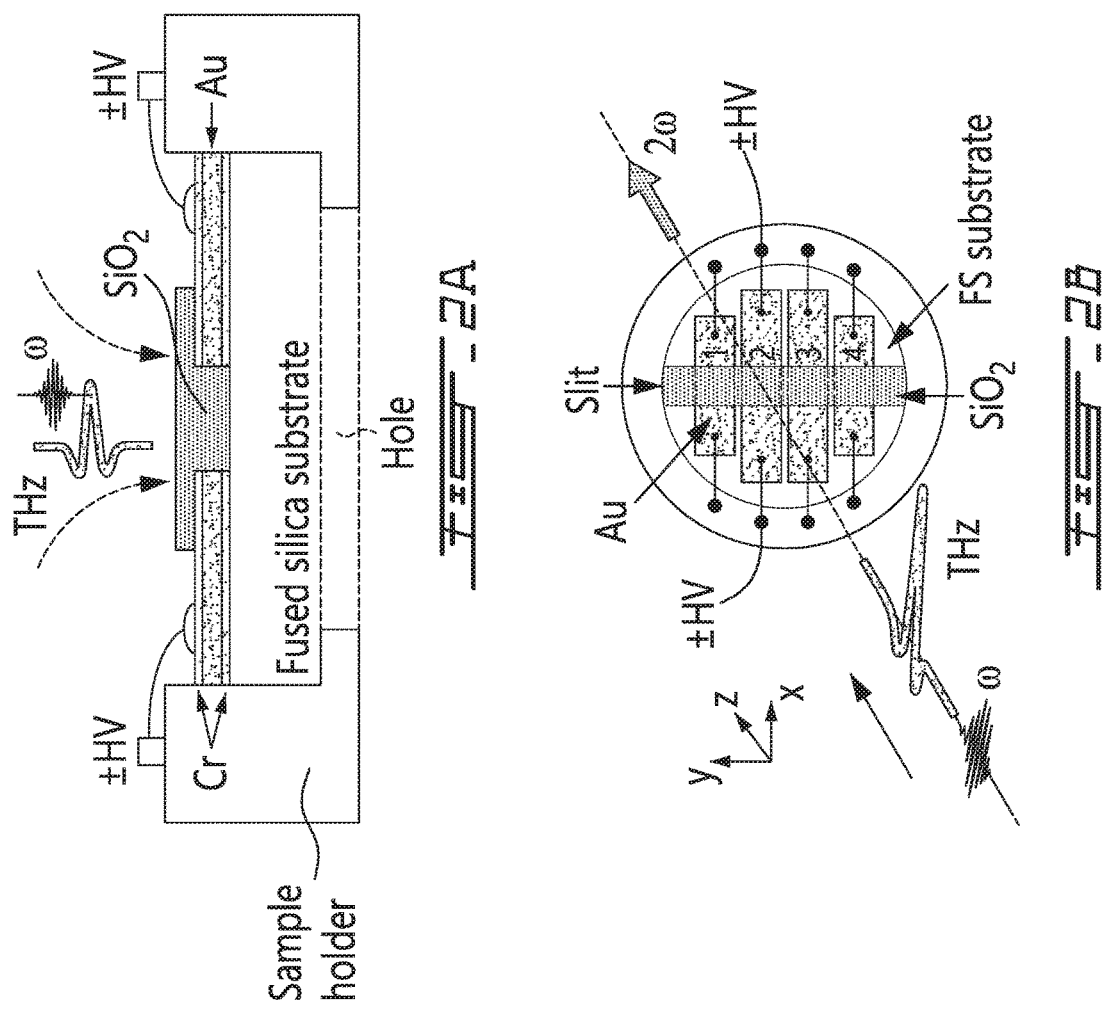

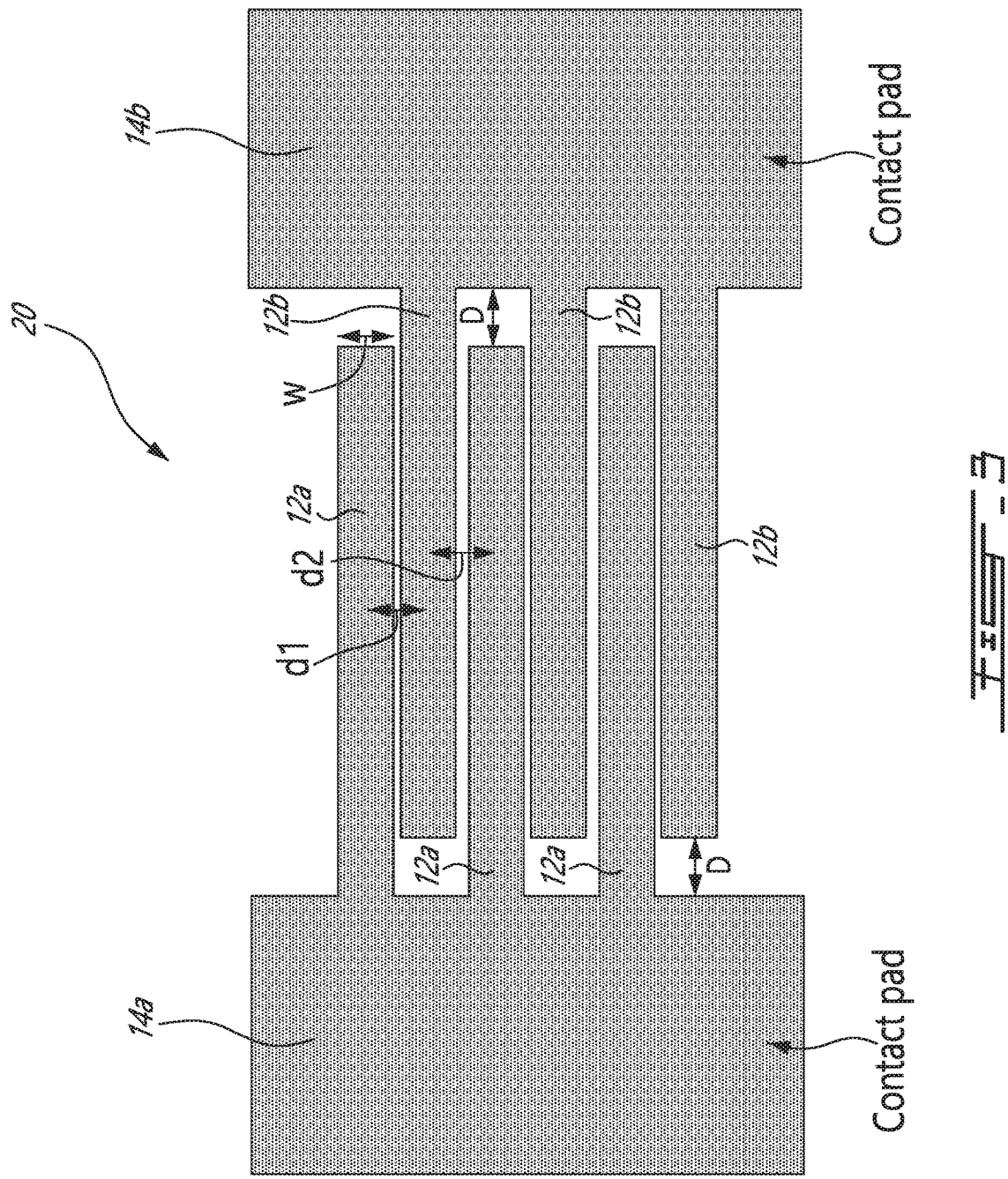

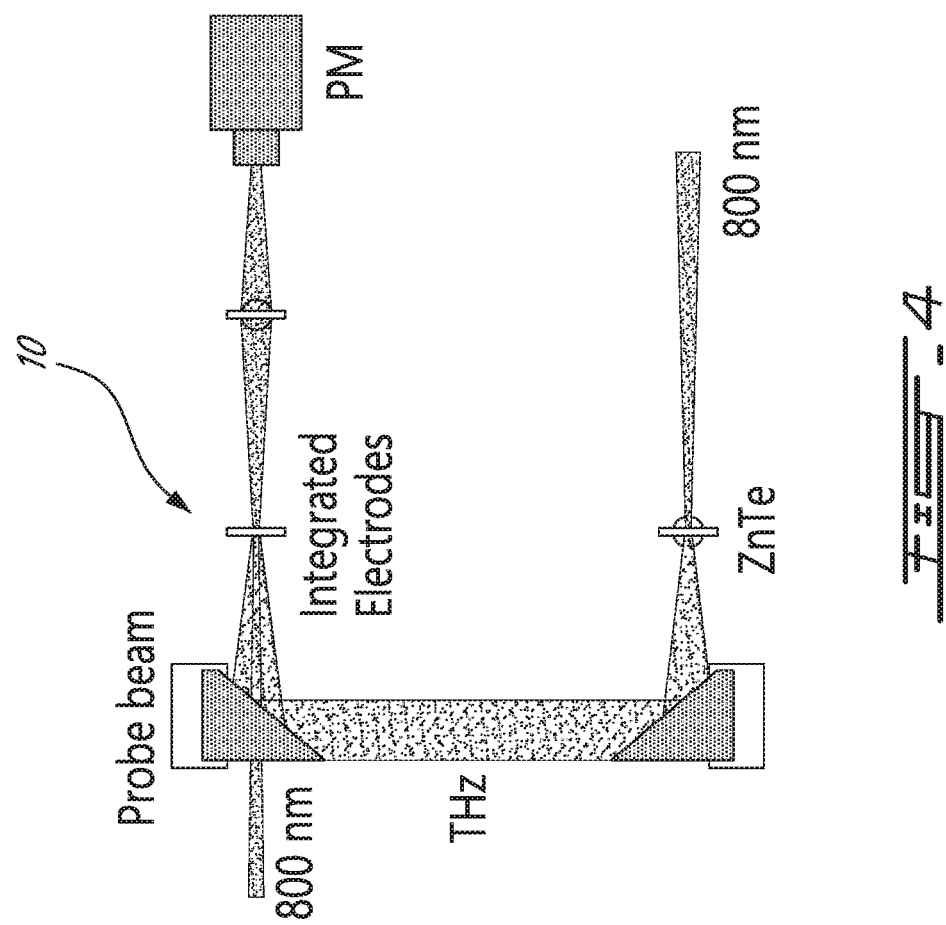

FULLY-COHERENT TERAHERTZ DETECTION METHOD AND SYSTEM

CROSS-REFERENCE TO RELATED APPLICATIONS

This application is a National Entry Application of PCT application no PCT/CA2015/050285 filed on Apr. 8, 2015 and published in English as WO 2015/154184 under PCT Article 21(2), which itself claims benefit of U.S. provisional application Ser. No. 61/977,736, filed on Apr. 10, 2014. All documents above are incorporated herein in their entirety by reference.

FIELD OF THE INVENTION

The present invention relates to a Terahertz (THz) detection. More specifically, the present invention is concerned with a method and a system for fully coherent heterodyne detection system at Terahertz (THz) frequencies.

BACKGROUND OF THE INVENTION

Photoconductive antennas (PCA) [1] and electro-optic (EO) crystals [2] are widely used as detectors for coherent measurement of THz fields. In both detection methods, a part, called the detection pulse, of the same ultrashort laser pulse that is used to generate the terahertz pulse is fed to the detector, where it arrives simultaneously with the terahertz pulse. The detector produces a different electrical signal depending on whether the detection pulse arrives when the electric field of the THz pulse is low or high. An optical delay line is used to vary the timing of the detection pulse.

Both methods, i.e. photoconductive detection and electro-optical sampling, suffer from a number of limitations. Indeed, in the case of photoconductive detection, it is well known that the lifetime of photo carriers in the semiconducting materials of a photoconductive detector limits the THz detection bandwidth. In the case of electro-optical sampling, the detection efficiency and bandwidth of electro-optic (EO) crystals is restricted by optical absorption at THz frequencies and by the phase mismatch associated to the optical rectification process underlying the detection process. Furthermore, THz fields of the order of few hundred kilovolts per centimeter can induce an over rotation of the probe polarization during EO sampling in mm length EO crystals, such as ZnTe for example, with a consequent distortion of the detected waveform.

It has been demonstrated that THz fields can be detected by nonlinear interaction in centrosymmetric media via the well-known electric-field-induced second-harmonic generation (EFISH) [3]. The same effect has been employed for probing millimeter-wave circuits [4] and for the measurement of liquid dynamics [5]. For THZ, it has been named terahertz-field-induced second harmonic generation or TFISH. Yet these measurements are not able to retrieve the amplitude and phase of the THz electric field and are hence incoherent.

More recently, TFISH has been employed as a tool for the coherent characterization of THz field. The beating of the TFISH signal with a local oscillator at the same frequency is used to map the THz electric field temporal trace. This was firstly observed for intense probe pulses generating supercontinuum at the TFISH wavelength [6].

A further optimization of this scheme, named Air Biased Coherent Detection (ABCD), relies on an external DC field to bias the THz-probe pulse interaction region, thus providing the required local oscillator signal [7]. Further developments have been proposed for air-based detection of ultrabroadband THz pulses via electric field induced second harmonic generation, such as direct injection of the local oscillator field [8] or the analysis of the THz-probe spectrogram.

The Air Biased Coherent Detection (ABCD) method, based on the Terahertz Field Induced Second Harmonics (TFISH) process occurring in ambient air (or selected gasses), allows recording Terahertz fields with extremely large bandwidth, i.e. above 20 THz, depending on the duration of the sampling pulse. However, miniaturization and integration remains a main concern. Indeed the existing systems cannot be easily miniaturized to the extent of a few centimeters. Furthermore these detection systems require the use of high voltage amplifiers, typically kV sources, thus limiting the use of the method. Moreover, since the detection occurs in air, the use of high voltage is limited by the air breakdown voltage.

The current systems for the Air Biased Coherent Detection (ABCD) method are composed of a pair of electrodes, suspended in air and typically separated by a distance of 1 millimeter, which corresponds to a region where THz and optical beams are focused. In this region, an external ac bias electrical field of about 2 KV, 500 Hz is typically applied to the optical focus in order to generate a bias optical field. The higher the external bias, the better the signal. The external ac bias electric field oscillates at a repetition rate that is half of the laser repetition rate. As the detection signal to noise ratio (SNR) depends on the amplitude of the bias field applied, high bias fields are necessary to obtain a good signal. Since the detection occurs in air, a first limitation is thus the air breakdown voltage ($3 \cdot 10^6$ V·m$^{-1}$), which is the maximum bias field that can be applied between the electrodes before the appearance of corona discharges leading to the breakdown of the system. Moreover, the method is also limited by the distance between the electrodes, which cannot be reduced for mechanical reasons. Furthermore, due to the low nonlinear coefficient of air, intense probe pulses are required, which can only be delivered by amplified systems, such as CPA (chirped pulse amplification) for example. These laser systems are expensive and feature large footprints, which considerably limits the accessibility of the method.

Thus there is still a need in the art for a method and system for a fully-coherent terahertz detection.

SUMMARY OF THE INVENTION

More specifically, there is provided a terahertz detection system, comprising at least a first and a second electrodes separated by a centro-symmetric material, and metallic contacts for connection to a voltage source.

There is further provided a terahertz detection system, comprising a terahertz beam source; a probe beam source; a detection unit comprising at least a first and a second electrodes separated by a centro-symmetric material connected to a low voltage source; and focusing optics adapted to overlap the terahertz beam and the probe beam and propagate them through the detection unit.

Three is further provided a method for terahertz detection, comprising generating a second harmonic beam by propagating overlapping probe and terahertz beams in a centrosymmetric material separating at least a first and a second electrodes connected to a voltage source.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 1 show steps of a method according to an embodiment of an aspect of the present invention;

FIG. 2A is a schematic view of a system according to an embodiment of an aspect of the present invention;

FIG. 2B shows a x-polarized optical probe pulse propagating through a metallic slit along the z-axis in the system of FIG. 2A;

FIG. 3 is a schematic view of a system according to an embodiment of an aspect of the present invention; and FIG. 4 is a schematical view of a THz generation and detection system according to an embodiment of an aspect of the present invention.

DESCRIPTION OF ILLUSTRATIVE EMBODIMENTS

The present invention is illustrated in further details by the following non-limiting examples.

FIG. 1 shows steps of a method 100 fabrication of a system according to an embodiment of an aspect of the present invention, in the case of two separate coplanar gold layers deposited on a 1 mm-thick UV graded fused silica substrate $SiO_2$.

A first layer of chromium is deposited on the UV graded fused silica substrate (step 120), then at least one gold layer is deposited on the layer of chromium (step 130), and a second layer chromium is deposited on top of the gold layer (step 140) in order to ensure a good contact of the gold electrodes with fused silica $SiO_2$. Electrodes are then defined by UV lithography and etching (step 150) forming a gap therebetween. Then, fused silica $SiO_2$ is deposited in the gap between the electrodes in order to fill it and to partially cover the electrodes (step 160) so that to avoid discharge in air. Finally pads intended for connection of the system to a high voltage source (HV) are opened by UV lithographic and etching (step 170).

Any kind of quartz wafer available on the market can be used as a substrate. The substrate has a typical thickness in a range comprised between about 0.5 and about 10 mm. The first chromium layer has a thickness selected in the range comprised between about 10 and 40 nm, for example 30 nm, and the gold layer has a thickness selected in the range comprised between about 40 and about 120 nm, for example 100 nm.

In step 150, by a UV photolithographic process, electrodes are defined by etching the whole layer of metal, i.e. chromium and gold, until the $SiO_2$ substrate. The distance between the electrodes is in the range between 5 nm and 100 μm, typically of a few tens of micrometers or less, for example 30 μm.

With a different process, such as e-beam lithography for example, the distance between the electrodes can be reduced below 1 μm. In this case improvement in the signal is expected, due to field-enhancement effects of the THz field in the gap between the electrodes.

As shown in FIG. 2, in a system 10, the gold electrodes are connected to a bipolar voltage modulator HV.

Doubly resonant structures 20, i.e. enhancing both the THz and the optical probe, such as interdigitated electrodes 12, may also be fabricated. FIG. 3 illustrates electrodes 12a supported by contact pad 14a interdigitated with electrodes 12b supported by contact pad 14b. In this case, the width (w) of each electrode 12a, 12b ranges between about 5 and about 100 micrometers. The electrodes 12a and 12b are positioned asymmetrically in order to avoid the generation of second harmonic with opposite phase which would induce the cancellation of the effect: each electrode is separated from a first electrode by a distance ($d_1$) selected in a range between 1 and 5 micrometers, and from a second electrode by a distance ($d_2$) in a range between 5 and 25 micrometers, with $d_2$ of the order of 3 to $6d_1$. The distance (D) between the end of each electrode 12a, 12b and the opposite contact pad 14b, 14a respectively is in the range between a few nanometers and about 10 micrometers. The small inter-electrode distance (d) allows increasing the applied bias and then enhances the electric field between the electrodes, which results in increasing the second harmonic SH signal and thus in improving the detection. Furthermore, the large area, related to width (w) and length between the contact pads, of the interdigitated electrodes 12a, 12b permits to work with much larger incident beams. The distance between the two opposite pads, i.e. the lengths of the electrode, can vary from hundreds of micrometers to few millimeters.

Any kind of metal contact for the pads can be used. The most common ones can be an alloy of Aluminium/Silicium, Gold/Chromium or simply Platinum, Graphite, Rhodium, Copper, Lead, Silver. The deposited metal may be part of a CMOS compatible process.

Diamond may be considered a centro-symmetric material of choice for the nonlinear medium due to its high nonlinear coefficient, good transparency properties at the wavelengths involved in the process and high breakdown voltage.

Graphite or graphene may be used for the electrodes, or conducting materials or conductive materials used for conduction, i.e. noble metal, metal oxide/hydroxide, carbon materials, and conductive polymers.

The substrate material use in the prototype was crystalline quartz. The substrate has to be transparent to THz frequencies and CMOS compatible such as for example high resistivity silicon, sapphire, crystalline quartz.

There is thus provided a system comprising conductive electrodes embedded in a centro-symmetric material, the distance separating the electrodes selected as short as 1 micrometer depending on the method used (see step 150 described hereinabove).

In a set up for THz detection according to an embodiment of an aspect of the present invention illustrated in FIG. 4 for example, THz radiation is generated via optical rectification from a Zinc Telluride (ZnTe) crystal and focused on a detection system 10 described hereinabove for example. A probe beam (800 nm) is focused in order to make it overlap with the generated THz beam. The x-polarized optical probe beam and the THz beam then propagate through the metallic slits and into the $SiO_2$ located between the gold electrodes along the z axis of the detection system 10. A bias field in a range between about ±10V and about ±300V, for example of ±250V, is applied between the electrodes, allowing generating a second harmonic beam. The signal is collected by a photomultiplier (PM), thus permitting to retrieve the amplitude and phase of the THz wave. It is to be noted that, in absence of a low voltage source, a voltage up to 1 kV may be applied between the electrodes without damaging the unit.

As people in the art may appreciate, detection systems of the present invention allow solving a number of problems identified in particular in the Air Biased Coherent Detection (ABCD) method at least for the following reasons.

First, a solid state dielectric material with a breakdown voltage or dielectric strength higher than that of air, which is about $3 \cdot 0 \; 10^6$ V·m$^{-1}$, for example theoretically three orders of magnitude higher in the case of silica $SiO_2$ with a value of about $10^9$ V·m$^{-1}$ at room temperature, can be selected, thus allowing reaching an excellent signal to noise ratio (SNR), of about 100 under an applied bias field of 250V and of about 50 under an applied bias field of 50V for example.

Secondly, since a small inter-electrode distance can be selected, in the range between 5 nm and 100 µm, the applied voltage can be significantly lower, i.e. in a range between a few volts to hundreds of volts i.e. between about ±10V and about ±300V, compared to about ±1000 V in the standard Air Biased Coherent Detection (ABCD) method, so that commercial low-voltage sources can be employed instead of more expensive high-voltage amplifiers.

Thirdly, when selecting a centro-symmetric material, such as fused silica $SiO_2$ in the above example, due to the high nonlinearity induced by the centro-symmetric material, commercially available fiber lasers may be used instead of expensive amplified laser systems delivering intense pulses.

Moreover, the present detection system can be miniaturized and integrated due to its compact size.

There is thus provided a detection system using metallic slits, for example one slit between two opposite electrodes as illustrated herein in FIGS. 1 and 2 for example, or multiple slits as illustrated herein in FIG. 3 for example, with a gap width in the range between about and 5 nm and about 100 µm, filled with a material having a high nonlinear index, i.e. from $n_2=10^{-16}$ cm$^2$/W (as for $SiO_2$ for example) to $n_2=10^{-7}$ cm$^2$/W (as for graphen for example), a high breakdown voltage i.e. of at least $10^9$ V·m$^{-1}$, such as fused silica in the example illustrated herein. The slits are biased with an external voltage source in order to generate a bias field the layer of nonlinear material that is deposited in the slits between the electrodes and to induce a second harmonic pulse.

The present detection system is thus a broadband terahertz detection system of reduced size compared to commercially available solutions. Furthermore, due the small inter-electrode distance, the required bias voltage can be significantly reduced with respect to commercially available solutions, and so the cost of the power supply as well. Since no high-voltage is required, the system is safer than similar commercially available solutions. The method of fabrication may be completely CMOS compatible, which is of interest in view of the production and commercialization of the system.

Moreover, it can be contemplated using, instead of an intense probe generally delivered by a Ti:sapphire laser, a fiber laser, which again reduces the price of the necessary equipment thus increasing the accessibility of the method to a large number of scientists and companies.

The scope of the claims should not be limited by the embodiments set forth in the examples, but should be given the broadest interpretation consistent with the description as a whole.

REFERENCES

[1] D. Grischkowsky, S. Keiding, M. Exter, C. Fattinger, J. Opt. Soc. B 7, 2006 (1990).
[2] Q. Wu, M. Litz, X.-C. Zhang, Appl. Phys. Lett. 68, 2924 (1996).
[3] A. Nahata, T. F. Heinz, Opt. Lett. 23, 67 (1998).
[4] C. Ohlhoff, C. Meyer, G. aipke, T. Lciffler, T. Pfeifer, H. G. Roskos, H. Kurz, Appl. Phys. Lett. 68, 1699-1701 (1996).
[5] D. J. Cook, J. X. Chen, E. A. Morlino, R. M. Hochstrasser, Chem. Phys. Lett. 309, 221 (1999).
[6] J. Dai, X. Xie, X.-C. Zhang, Phys. Rev. Lett. 97, 103903 (2006).
[7] N. Karpowicz, J. Dai, X. Lu, Y. Chen, M. Yamaguchi, H. Zhao, X.-C. Zhang, L. Zhang, C. Zhang, M. Price-Gallagher, C. Fletcher. O. Mamer, A. Lesimple, K. Johnson, Appl. Phys. Lett. 92, 011131 (2008).
[8] C. Y. Li, D. V. Seletskiy, M. Sheik-Bahae, CLEO conference: Science and Innovations San Jose, Calif. United States Jun. 9-14, (2013).

The invention claimed is:

1. A terahertz detection system, comprising at least a first and a second electrodes separated by a centro-symmetric material, said electrodes having metallic contacts for connection to a voltage source, said voltage source being adapted to provide a bias field between said electrodes to said centro-symmetric material, said system inducing a second harmonic beam by propagation and overlapping of a probe and a terahertz beams in said centro-symmetric material.

2. The detection system of claim 1, wherein said centro-symmetric material has a nonlinear index comprised between about $10^{-16}$ cm$^2$/W and $10^{-7}$ cm$^2$/W and a breakdown voltage of at least $10^9$ V·m$^{-1}$.

3. The detection system of claim 1, wherein said electrodes are separated by a distance in a range between 5 nm and 100 µm.

4. The detection system of claim 1, wherein said material is fused silica.

5. The detection system of claim 1, wherein said material is diamond.

6. The detection system of claim 1, wherein said electrodes are made in one of a noble metal, a metal oxide, a metal hydroxide, a carbon material and a conductive polymer.

7. The detection system of claim 1, wherein said electrodes are made of one of graphite and graphene.

8. The detection system of claim 1, wherein said electrodes are coplanar gold layers deposited on a graded fused silica substrate, and said material is fused silica.

9. The detection system of claim 1, wherein said electrodes are coplanar gold layers deposited on a graded fused silica substrate via a chromium layer.

10. The detection system of claim 1, wherein said electrodes are coplanar gold layers of a thickness in a range comprised between about 40 and about 120 nm deposited on a graded fused silica substrate of a thickness in a range comprised between about 0.5 and about 10 mm via a chromium layer of a thickness selected in the range comprised between about 10 and 40 nm.

11. The detection system of claim 1, comprising at least a first and a second electrodes supported by a first contact pad interdigitated with a third and a fourth electrodes supported by a second contact pad facing said first contact pad, said first and said third electrodes being separated by a first distance, said third electrode and said second electrode being separated by a second distance, and said third electrode and said second electrode being separated by the first distance, the first distance being selected in a range between 1 to 5 micrometers, the second distance being selected in a range between 5 to 25 micrometers, and said second distance being of the order of 3 to 6 times said first distance.

12. The detection system of claim 1, wherein said voltage source is adapted to provide a bias field in a range between ±10V and ±300V.

13. A terahertz detection system, comprising:
- a terahertz beam source;
- a probe beam source;
- a detection unit comprising at least a first and a second electrodes separated by a centro-symmetric material;
- focusing optics adapted to overlap the terahertz beam and the probe beam and propagate them through the detection unit; and
- a voltage source adapted to provide a bias field between said electrodes to said centro-symmetric material, inducing a second harmonic beam by propagation and overlapping of the probe and the terahertz beams in said centro-symmetric material.

14. A method for terahertz detection, comprising generating a second harmonic beam by propagating overlapping probe and terahertz beams in a centro-symmetric material separating at least a first and a second electrodes connected to a voltage source adapted to provide a bias field between said electrodes to said centro-symmetric material.

* * * * *